US00PP19043P3

(12) United States Plant Patent

Anderson et al.

(10) Patent No.: US PP19,043 P3

(45) Date of Patent: Jul. 22, 2008

(54) *CHRYSANTHEMUM* PLANT NAMED '95-169-8'

(50) Latin Name: *Dendranthema×hybrida*
Varietal Denomination: 95-169-8

(75) Inventors: Neil O. Anderson, St. Paul, MN (US); Peter Ascher, Bowler, WI (US)

(73) Assignee: Regents of the University of Minnesota, St. Paul, MN (US)

( * ) Notice: Subject to any disclaimer, the term of this patent is extended or adjusted under 35 U.S.C. 154(b) by 0 days.

(21) Appl. No.: 11/811,768

(22) Filed: Jun. 12, 2007

(65) Prior Publication Data

US 2007/0289037 P1 Dec. 13, 2007

Related U.S. Application Data

(60) Provisional application No. 60/812,821, filed on Jun. 12, 2006.

(51) Int. Cl.
*A01H 5/00* (2006.01)

(52) U.S. Cl. ..... Plt./286

(58) Field of Classification Search ..... Plt./286
See application file for complete search history.

*Primary Examiner*—Kent L. Bell

(74) *Attorney, Agent, or Firm*—Penny J. Aguirre

(57) ABSTRACT

A new cultivar of chrysanthemum, '95-169-8', characterized by it's frost tolerant quadriplex daisy-type inflorescences with red ray florets and bright yellow disk florets, its vigorous shrub-like growth habit after two years of growth, its tight cushion plant form attained without pinching, and its good garden performance and winter hardiness.

2 Drawing Sheets

STATEMENT REGARDING FEDERALLY SPONSORED RESEARCH

This invention was made with government support under MIN-21-50 and MIN-21-52 awarded by the U.S. Dept. of Agriculture. The government has certain rights in the invention.

Botanical classification: *Dendranthema×hybrida.*

Variety denomination: '95-169-8'.

BACKGROUND OF THE INVENTION

The present invention relates to a new and distinct cultivar of garden chrysanthemum plant, botanically known as *Dendranthema×hybrida* '95-169-8' and will be referred to hereinafter by its cultivar name, '95-169-8'. The new cultivar is commercially known as a garden-type chrysanthemum.

'95-169-8' was derived from an on going controlled breeding program that focuses on obtaining new cultivars of garden chrysanthemums in a range of flower colors that exhibit superior winter hardiness for northern climates, a large shrub-like habit in successive growth years that, and a tight cushion plant habit without the need for pruning or pinching. The breeding originally commenced with crosses utilizing *Dendranthema weyrichii* 'Pink Bomb' (not patented) and various unpatented cultivars of *Dendranthema×grandiflora.*

The new cultivar, '95-169-8' was created with a series of crosses and selections made over a period of years between 1990 and 1994 utilizing proprietary selections, '95-169-8' was ultimately derived from a cross-pollination made in 1994 the female parent '92-333-2' (U.S. Plant Pat. No. 14,197) and the male parent 'Mirage' (U.S. Plant Pat. No. 6,388). The new chrysanthemum was selected as a single plant within the progeny of the stated cross in 1995 by the inventors in St. Paul, Minn. '95-169-8' was selected as unique for its quadriplex daisy-type inflorescences with red ray florets and bright yellow disk florets combined with the characteristics that fit the objectives of the breeding program.

Asexual reproduction of the new cultivar was first accomplished via stem cuttings in St. Paul, Minn. in 1995. The characteristics of this cultivar have been determined to be stable and are reproduced true to type in successive generations.

Comparisons: '92-333-2', the female parent, is similar in flower color and plant habit, however '95-169-8' blooms earlier and has flowers that are more greyed in color when mature. 'Mirage', the male parent, differs in plant habit and has pompom type flowers that are orange-bronze in color. The closest comparison cultivar known to the invention is 'Dark Grendaine' (U.S. Plant Pat. No. 7,632). 'Dark Grenadine' has flowers that are similar in color, however, it lacks the spreading and prolific plant habit and massive flower display that is characteristic of '95-169-8' in the second and subsequent years of growth.

SUMMARY OF THE INVENTION

The following traits have been repeatedly observed and are determined to be the characteristics of the new cultivar of chrysanthemum. These attributes in combination distinguish '95-169-8' as unique from all other varieties of chrysanthemum known to the inventors.

1. '95-169-8' is early blooming and exhibits quadriplex daisy-type inflorescences with red to red-grey ray florets and bright yellow disk florets. The slight grey tones give the flowers a unique coloration.
2. '95-169-8' attains a large shrub-like habit in the second and successive years of growth attaining about 45 to 53 cm in height the first year and about 76 to 106 cm in height and 83 to 152 cm in width in the second year.

3. '95-169-8' forms a tight cushion plant form without the need for pinching or pruning.
4. '95-169-8' exhibits extreme hybrid vigor.
5. '95-169-8' exhibits a massive floral display in its second and subsequent years after planting.
6. '95-169-8' is a winter hardy shrub chrysanthemum with hardiness to U.S.D.A. Zone 3.
7. The inflorescences of '95-169-8' are frost tolerant.

BRIEF DESCRIPTION OF THE DRAWINGS

The accompanying colored photographs illustrate the overall appearance and distinct characteristics of the new chrysanthemum. The photographs were taken of plants grown for two years under field conditions in Waseca, Minn.

Figure 1:
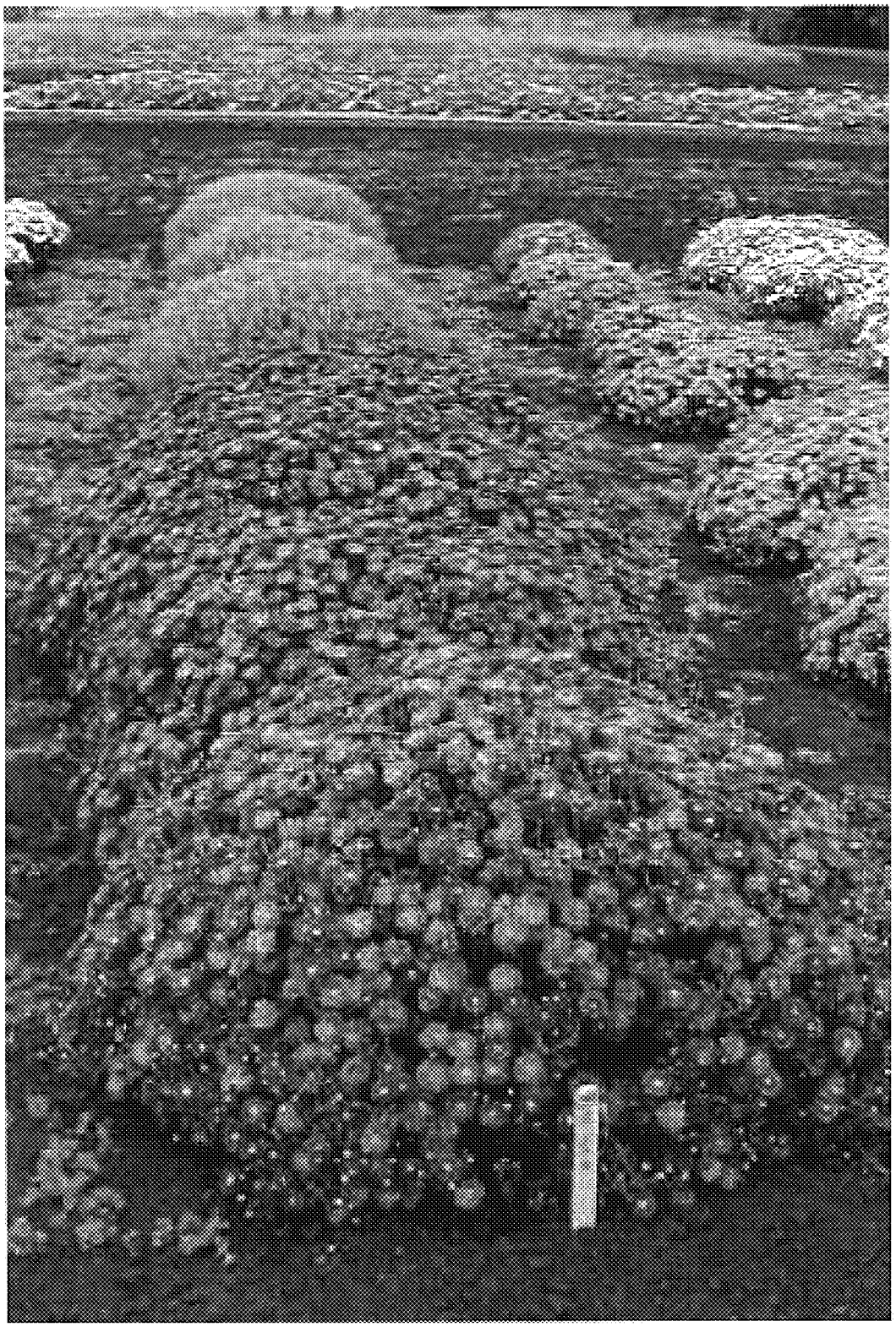
FIG. 1 is a photograph of a row of '95-169-8' plants.
Figure 2:
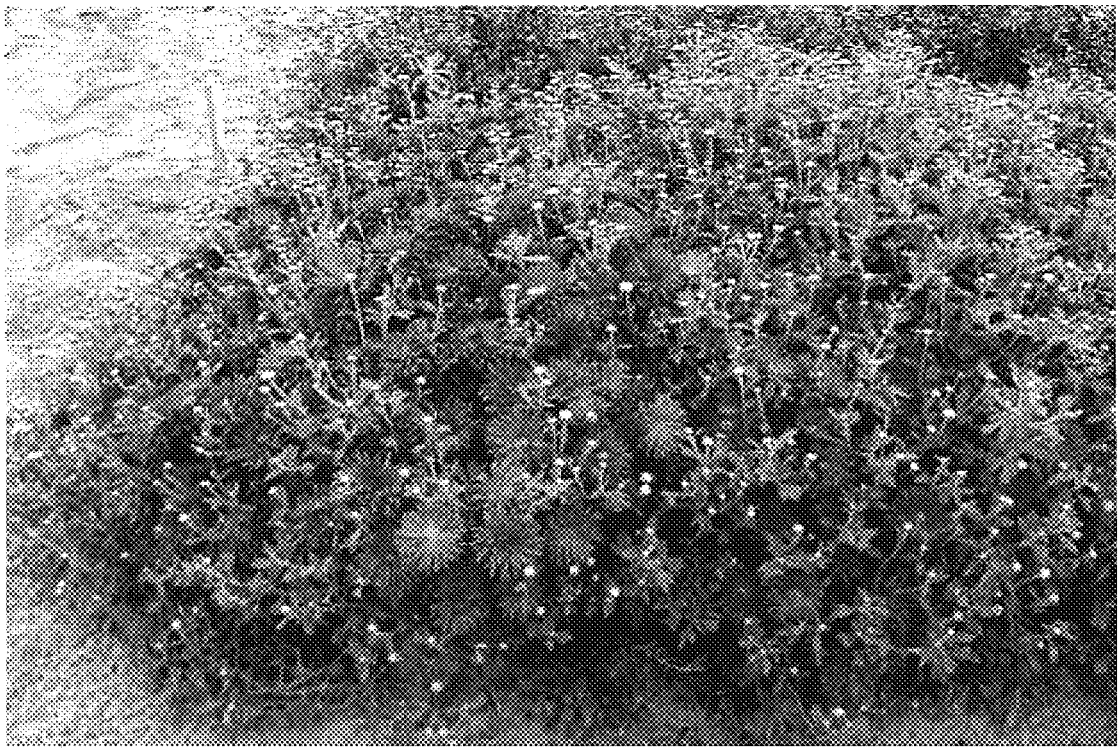

The photograph in FIG. 2 provides a view of a single plant of '95-169-8'.

The colors in the photographs are as close as possible with the photographic and printing technology utilized. The color values cited in the detailed botanical description accurately describe the colors of the new chrysanthemum.

DETAILED BOTANICAL DESCRIPTION

The following is a detailed description of the new cultivar as grown outdoors under natural lighting in a trail bed in St. Paul, Minn. and observed over a period of five years. The color readings were taken on Jan. 18$^{th}$, 2001 from plants of grown from cuttings under greenhouse conditions that are typical of commercial production. Plants were grown under approximately 2,500 footcandles of light and temperatures of approximately 72° F. during the day and 65° F. during the night. The phenotype of the new cultivar may vary with variations in environmental, climatic, and cultural conditions, as it has not been tested under all possible environmental conditions. The color determination is in accordance with the R.H.S. Colour Chart of The Royal Horticultural Society, London, England, except where general color terms of ordinary dictionary significance are used.

General description:

*Blooming season.*—Early flowering commencing in late August.

*Plant habit.*—Herbaceous perennial, mounded habit, produces a cushion form in the first year of growth, attains a larger shrub-like habit in the second and subsequent years with a tight cushion plant form.

*Height and spread.*—Reaches about 45 to 53 cm in height the first year and about 76 to 106 cm in height and 83 to 152 cm in width in the second and subsequent years.

*Hardiness.*—U.S.D.A. Zone 3.

*Diseases resistance.*—No susceptibility or resistance to diseases common to chrysanthemum has been observed.

*Root description.*—Fibrous.

Growth and propagation:

*Propagation.*—Terminal stem cuttings.

*Time to root initiation.*—About 1 week.

*Crop maintenance.*—No pinching or pruning is required to achieve the cushion plant habit and abundant bloom.

*Growth rate.*—Vigorous.

Stem description:

*Stem color.*—145A.

*Lateral branch length.*—Range of 16 to 36 cm.

*Lateral branch diameter.*—Average of 2.5 mm.

*Quantity of lateral branches.*—Average of one lateral branches produced per node when apical meristem is removed (pinched).

*Internode length.*—Average of 1.3 cm.

Foliage description:

*Leaf division.*—Simple.

*Leaf shape.*—Blade is ovate in outline with narrow region extending towards base.

*Leaf base.*—Cuneate.

*Leaf apex.*—Truncate and dentate.

*Leaf margin.*—Incised (mulberry-like incisions).

*Leaf venation.*—Upper surface 138B, lower surface 138C

*Leaf attachment.*—Sessile.

*Leaf arrangement.*—Alternate.

*Leaf number.*—Range from 5 to 23 per lateral branch.

*Leaf surface.*—Slightly hirsute on upper and lower surface.

*Leaf color.*—Young foliage; upper surface 138A, lower surface 138B, mature foliage; upper surface 137B, lower surfaces 138B.

*Leaf size (fully expanded).—Average of* 8.5 cm in length and 3.7 cm in width.

*Fragrance of foliage.*—Fragrant if bruised.

Flower description:

General description:

*Inflorescence type.*—Composite, quadriplex daisy.

*Flowering response.*—6 weeks of short days.

*Lastingness of inflorescence.*—Temperature dependent, under normal field conditions during the fall, flowers typically last about 2 to 4 weeks, although flowering of the entire plant extends from 7 to 10 weeks.

*Fragrance.*—None.

*Quantity of inflorescences.*—About 3,000 to 4,000 flowers per plant in second year.

*Inflorescence buds.*—About 8 mm in depth and 1.1 cm in diameter, inverted funnel shaped, color 23D.

*Inflorescence size.*—About 1.5 cm in depth and 5 cm in diameter, diameter of disk about 1 cm.

*Peduncle.*—Stiff, held at an angle of 45° to stem, texture is slightly hirsute, first peduncle is an average of 1.9 cm in length and fourth peduncle is an average of about 3.5 cm in length, color is 138B.

*Involucral bracts (phyllaries).*—Crenulate in appearance, 138A in color, about 2 to 5 mm in length, less than 1 mm in width, glabrous in texture.

Ray florets (capitulate):

*Number.*—About 48.

*Shape.*—Linear lanceolate.

*Aspect.*—Outer are reflexed, inner are upright.

*Size.*—Average of 2.4 cm in length and 6 mm width.

*Petal apex.*—Rounded.

*Petal base.*—Aequilateral.

*Petal margins.*—Entire.

*Petal texture.*—Glabrous and silky on upper and lower surfaces.

*Petal color.*—Opening; Upper surface 60A, lower surface 184B, fully open; upper surface 181A, lower surface 173D, fading; upper and lower surface 182A.

Disk florets (perfect):

*Quantity.*—About of 101.

*Shape.*—Tubular, rounded at tip.

*Size.*—About 5 mm in length and 1 mm in width when mature.

*Color.*—Immature 16A and mature 15A.

Reproductive organs:

*Presence.*—Disk flowers are perfect, ray flowers are carpellate.

*Gynoecium.*—1 Pistil per disk and ray floret, style color 7A.

*Androcoecium.*—1 stamen per disk floret, fused into tube surrounding style, anther color 21A, pollen fairly abundant, and 21A in color.

*Fruit and seed.*—About 150 ovules per floret. Fruit is an achene with a single seed attached to the ovary wall. Seed lacks pappus, have a compressed oval shape with pointed ends, are about 2 to 5 mm in length and 1 to 2 mm in width with a ridged texture and 200D in color.

We claim:

1. A new and distinct variety of chrysanthemum plant designated '95-169-8' as described and illustrated herein.

* * * * *